United States Patent

Johnson

| | |
|---|---|
| [11] Patent Number: | 5,667,512 |
| [45] Date of Patent: | Sep. 16, 1997 |

[54] PATELLAR RESECTION GUIDE

[75] Inventor: Wesley Johnson, Chanhassen, Minn.

[73] Assignee: Metagen, LLC, Menomonie, Wis.

[21] Appl. No.: 642,696

[22] Filed: May 3, 1996

[51] Int. Cl.⁶ ................................................ A61B 17/56
[52] U.S. Cl. ........................................ 606/88; 606/87
[58] Field of Search ........................ 606/79, 86, 87, 606/88

[56] References Cited

U.S. PATENT DOCUMENTS

| 4,335,715 | 6/1982 | Kirkley | 606/87 |
| 4,349,018 | 9/1982 | Chambers | 606/88 |
| 4,421,112 | 12/1983 | Mains et al. | 606/88 |
| 4,565,191 | 1/1986 | Slocum | 606/87 |
| 4,633,862 | 1/1987 | Petersen | 606/88 |
| 4,706,660 | 11/1987 | Petersen | 606/86 |
| 4,757,810 | 7/1988 | Reese | 606/82 |
| 5,002,547 | 3/1991 | Poggie et al. | 606/88 |
| 5,021,056 | 6/1991 | Hofmann et al. | 606/86 |
| 5,053,039 | 10/1991 | Hofmann et al. | 606/87 |
| 5,108,401 | 4/1992 | Insall et al. | 606/79 |
| 5,116,338 | 5/1992 | Poggie et al. | 606/90 |
| 5,246,444 | 9/1993 | Schreiber | 606/87 |
| 5,486,177 | 1/1996 | Mumme et al. | 606/79 |
| 5,542,947 | 8/1996 | Treacy | 606/88 |

*Primary Examiner*—Michael Buiz
*Assistant Examiner*—David O. Reip
*Attorney, Agent, or Firm*—Fredrikson & Byron, PA

[57] ABSTRACT

A patella resection guide. The guide includes a cradle having spaced cradle supports to support the quadriceps tendon and patella ligament and properly locate the patella. The resection guide also may have opposed, movable plates between which may be gripped lateral and medial surfaces of a patella. One of the plates may include a saw guide for guiding a bone saw in a resection procedure. The guide may employ manually operable threaded connections to facilitate drawing the plates together to grip between them a patella to be resected.

29 Claims, 7 Drawing Sheets

PATELLAR RESECTION GUIDE

FIELD OF THE INVENTION

The present invention relates to apparatus and methods for its use during orthopaedic surgery. More particularly, it is directed to apparatus and methods used to enable a surgeon to precisely resect or trim a patella in connection with knee joint replacement procedures.

BACKGROUND OF THE INVENTION

Surgical procedures to replace a complete or partial knee joint with a prosthetic implant are becoming increasingly common, with high rates of success. Total joint replacement is usually performed to relieve pain and restore function caused by damaged or malfunctioning joints.

In addition to replacing the diseased natural knee with femoral and tibial prostheses, the knee joint replacement procedure typically involves resurfacing the articular surface of the patella because in some cases the natural bone of the patella does not interface well with the materials used in constructing the prosthesis, and this can result in great pain to the patient. In most cases, the patella is resurfaced with a prosthetic component, or patellar button which may be made from ultra high molecular weight polyethylene.

Implantation of resurfacing components to the patella, in combination with the prosthetic knee joint if improperly aligned, can result in an undesirable alteration of the load distribution imparted to the prosthesis and supporting bone structures. Normal daily activity, such as walking, causes flexion and extension of the quadriceps mechanism, patellar ligament, and associated tendons. These movements in turn exert loads on the attached and surrounding anatomical or prosthetic structures.

In total knee joint replacement, it is critical to achieve uniform and properly oriented load transfer from the implant to the supporting bone. To accomplish this, it is desirable to recreate the loading patterns which are imparted to the supporting bone prior to placing the implants, as occurs in a normal, naturally functioning knee. These loading patterns are primarily compressive and adverse bone remodelling can result if atypical loading patterns, including shear, are introduced in the total knee procedure. It is thus desirable to accurately orient the implants to recreate normal stress patterns in supportive bony structure. When the patella is properly resected, the resultant force active on the patella will be generally perpendicular to the main plane of the patella, resulting in primarily compressive forces being imparted to the supporting bone. In this manner, the desired loading patterns may be recreated, imparting primarily compressive loads on the supporting bone to imitate the normal, natural condition.

Several devices are known in the prior art for resecting the articular surface of the patella. These commonly involve pliers or scissors-like mechanisms which grasp the patella. The surgeon is required to orient the patella in the device by visual approximation, relying on judgment for proper positioning and orientation. Available resection guides do not provide a reference to bony or soft tissue structures. The patella is then resected by placing a saw through the resection guide and sawing the patella. In the event of inaccurate or improper orientation of the patella within the device, the depth or angle of resection will be incorrect. This will result in an improper distribution of forces to the new knee joint, and adverse loading of the supporting bone structures may result.

What is clearly needed, therefore, is a device and method which will aid the surgeon in establishing an accurate and repeatable orientation of the patella during a resection procedure so as to enable proper orientation of a subsequently implanted patellar implant.

SUMMARY OF THE INVENTION

The present invention makes use of a device which is capable of offering the surgeon great precision, simplicity and reliability in resecting or trimming the patella as required in knee replacement surgery. In one embodiment, the invention provides a patella resection guide comprising a body carrying a pair of parallel cradle surfaces spaced so as to encounter and support respectively the posterior surfaces of the quadriceps tendon and the patella ligament of a patella received between the cradle surfaces. The parallel cradle surfaces define a reference plane, and the resection guide includes means for resecting the patellar at a desired orientation with respect to the reference plane.

In another embodiment, the invention comprises a patella resection guide that comprising gripping means including a pair of gripping elements having respective confronting gripping surfaces spaced to receive and grip a patella between them. Means are provided for supporting the gripping elements and maintaining the orientation of the gripping surfaces while enabling them to be advanced toward each other to grip a patella between them. At least one of the gripping elements includes saw guide means for guiding a bone saw during resection of a patella gripped between the gripping surfaces.

In a specific embodiment, the invention comprises a cradle designed to support posterior surfaces of the quadriceps tendon and patellar ligament during resection procedures. The cradle also acts as a frame to mount the gripping elements and permit them to move together and apart. Different sized cradles and plates are contemplated and within the scope of the invention. On either side of the cradle and opposing each other are the gripping elements which may be in the form of movable plates which act to secure the patella in the device. Means are also provided to advance or retract, and to secure and lock the position of the plates.

In yet another embodiment, the invention relates to a method for resecting a patella in which the patella, quadriceps tendon and patellar ligament are first surgically exposed. A resection guide is provided, the guide including a saw blade guide such as a slot. The resection guide has parallel cradle surfaces defining a reference plane and spaced to encounter posterior surfaces of the quadriceps tendon and the patella ligament of the patellar to support the patella in a fixed orientation with respect to the reference plane. The resection guide includes means for gripping and holding the patella in that orientation. In the method of this embodiment, the patella is supported in the resection guide with the cradle surfaces contacting and supporting respectively the posterior surfaces of the quadriceps tendon and patellar ligament. The patella is then gripped in that orientation, and the patella is resected with a bone saw guided by the saw guide.

In a preferred embodiment, the patella is resurfaced in the course of performing total knee replacement surgery. An incision is made which runs medial to the patella and which exposes the patella and attached quadriceps tendon and patella ligament structures. The patellofemoral joint is disarticulated, following which the patella is rotated laterally. This exposes the inner or articular surface of the patella. Next, the patellar resection guide of the invention is placed over the exposed articular surface of the patella. When this step is complete, the patella and resection guide together are reversed again, the patella being suspended between the parallel cradle supporting surfaces.

At this point, the guide is positioned between the patella and the femur, with the patellar ligament and quadriceps tendon suspended in the cradle support of the patellar resection guide. The knee is then slightly bent to draw the posterior surfaces of the quadriceps tendon and ligament firmly against the cradle surfaces and into the resection guide. The gripping elements are then drawn toward each other, firmly securing between them the patella. With the patella thus secured, the patella and guide are re-rotated to expose the articular surface of the patella. The resection procedure is performed at this stage through the use of an oscillating saw guided by the saw guide. Following resection of the patella and removal of the resection guide, established procedures may be followed to prepare the resected surface of the patella for reception of an implant or patellar button.

DETAILED DESCRIPTION OF THE PREFERRED EMBODIMENTS

Figure 1:
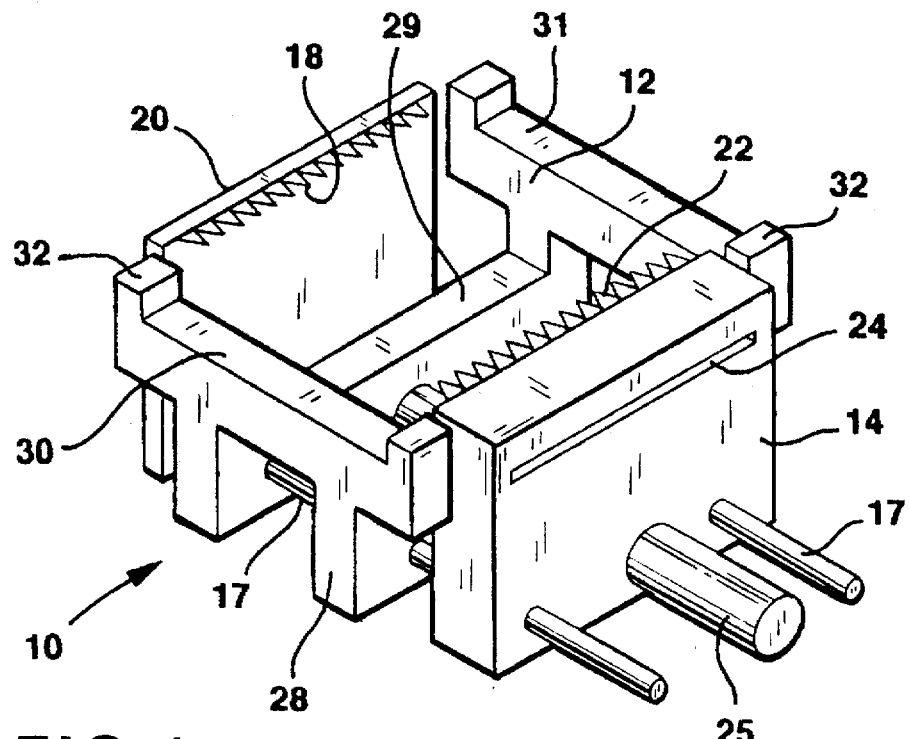
FIG. 1 is a perspective view, partially exploded, of a patellar resection guide of the present invention.
Figure 2:
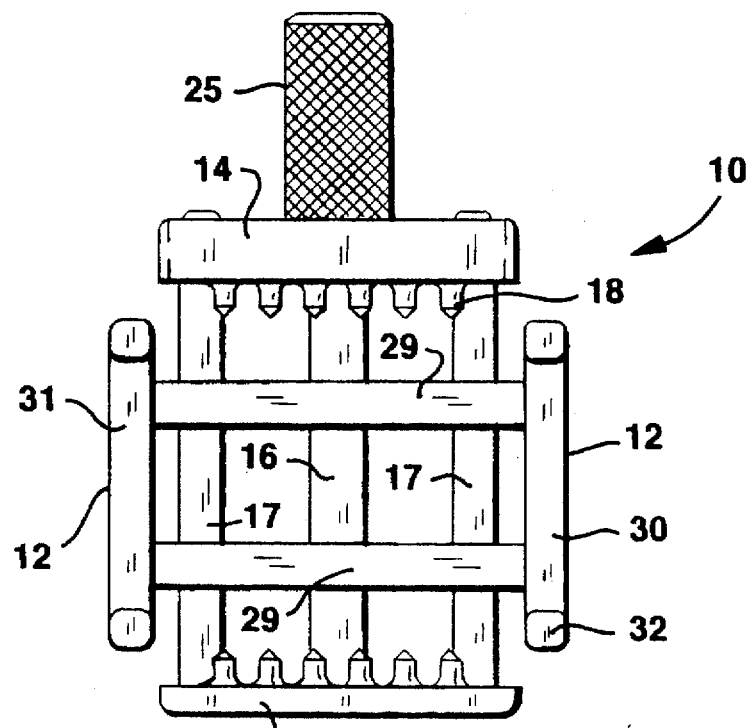
FIG. 2 is a top view of the assembled patellar resection guide of FIG. 1.
Figure 3:
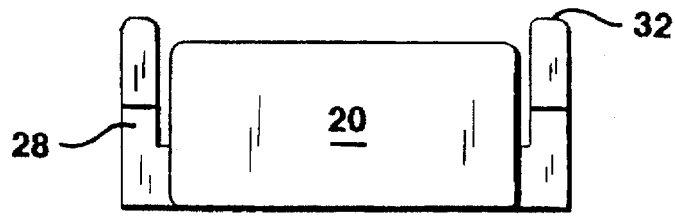
FIG. 3 is an end view of the patellar resection guide of FIG. 1.
Figure 4:
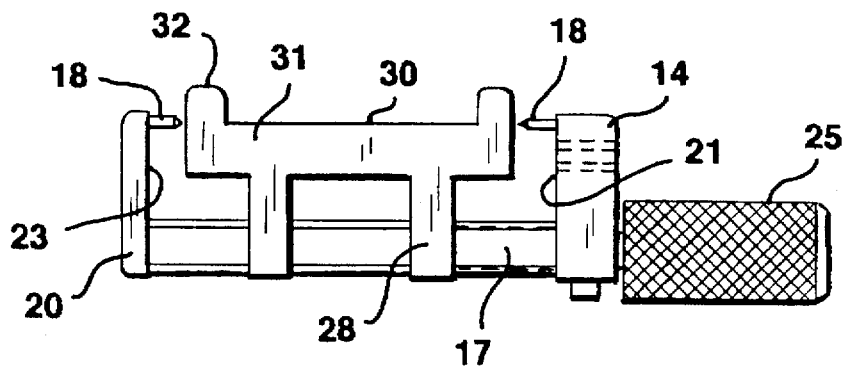
FIG. 4 is a side view of the patellar resection guide of FIG. 1.

With reference first to FIG. 1, a patellar resection guide is designated 10, and comprises a cradle 12 and a pair of gripping elements such as plates 14, 20. The cradle 12 is used to suspend the patella in a desired orientation established by supporting posterior surfaces of the quadriceps tendon and patellar ligament between the surfaces of spaced, parallel first and second cradle supports 30, 31, locating the articular surface of the patella in a position where it can be accessed by the surgeon's bone saw blade for resection.

The gripping plates comprise a blade guide plate 14 and a stop plate 20, both generally rectangular in shape and having patella gripping surfaces 21, 23. The gripping plates are sized and positioned to fit between the cradle supports 30, 31 to permit adjustable positioning of the distance between their respective gripping surfaces. The cradle supports 30, 31 are joined by a body defined by cross members 29. An adjustment bolt 16 passes through an aperture 36 in the cross members 29 of the cradle 12, as do two guide rods 17 arranged in parallel with the adjustment bolt 16. One or more saw blade slots 24 are formed through the blade guide plate 14 at positions designed to represent the proper depth required for resecting the articular surface of the patella.

Stop plate 20 is positioned with its gripping surface 21 opposed to and confronting the gripping surface 23 of the guide plate 14, the surfaces 21 and 23 desirably being parallel. Adjustment bolt 16 passes through the apertures 36 in the cross members 29 of the cradle 12, and guide rods 17 pass snugly through the apertures 34 in the cross members 29 and through the apertures 35 in the blade guide plate 14 to allow for controlled, supportive convergent and divergent travel of the blade guide plate 14 and stop plate 20. Blade guide plate similarly possesses an aperture 33 sized to receive adjustment bolt 16. Stop plate 20 is of similar size and shape to the blade guide plate 14, but may or may not contain a slot for guiding a saw blade. Stop plate 20 may be shallower in depth than blade guide plate 14. Adjustment bolt 16 and guide rods 17 are rigidly affixed to the stop plate 20. Adjustment bolt 16 is threaded from the portion extending from its free end to a point toward the stop plate 20 where the size limitations of the patella or cradle 12 obviate the need for further threading. When the stop plate 20 and affixed adjustment bolt 16 and affixed guide rods 17 are fitted through apertures 36, 34 in the cross members 29 forming the base of cradle 12, the blade guide plate 14 confront each other, as shown in FIG. 1.

Figure 11:
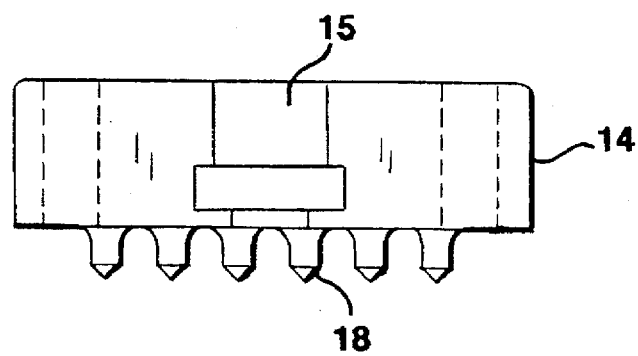
FIG. 11 is a bottom view of a blade guide plate showing a T shaped channel to accommodate the removable captured nut shown in FIG. 10.

Referring to FIG. 11, the blade guide plate 14 has a T shaped channel 15 cut into its bottom side to receive a nut 19 that is threaded onto the adjustment bolt 16. The nut is restrained by the walls of the crossbar portion of the T channel from movement parallel to its axis, and includes a tubular portion exuding through the leg of the T and terminating in an external, preferably knurled handle 25. Manual rotation of the handle 25 rotates the nut upon the threaded portion of the bolt to cause the blade guide plate 14 and stop plate 20 to be selectively moved toward and away from each other to accommodate and secure various sized patellae which may be encountered. The guide rods 17 ensure parallel movement of the blade guide plate 14 and stop plate 20. The gripping surfaces 21, 23 of the blade guide plate 14 and stop plate 20 may be provided with teeth 18, 22 or other irregular surfaces to facilitate grasping of the patella during the resection procedure.

Figure 5:
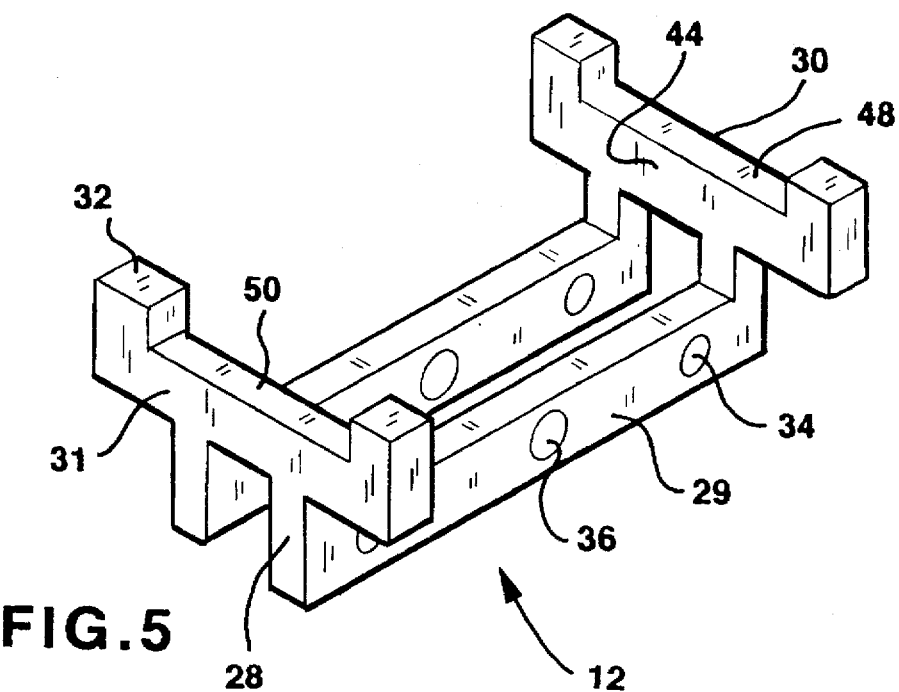
FIG. 5 is a perspective view of a cradle of the patellar resection guide shown in FIGS. 1–4.

As shown in FIG. 5, the supports 30, 31 have at their distal ends angled end portions that define end stops 32, the latter preferably being substantially at right angles to the cradle supports 30, 31. The cradle supports 30, 31 are connected in a substantially perpendicular manner to upright members 28. The upright members 28 are connected at substantially right angles to cross members 29. Cradle 12 is substantially symmetrical in configuration and serves as the framework for the other components of the invention. The patellar resection guide 10 quickly disassembles for easy cleaning or replacement of components.

Cradle 12 is provided with apertures 34, 36 which are adapted so as to slidably receive the guide rods 17. Aperture 36 is adapted to slidably receive adjustment bolt 16. Apertures 34, 36 are sized to allow blade guide plate 14 and stop plate 20 to adjust the distance from each other which will occur with rotating the adjustment nut 16. Tolerances between apertures 34, 36 and the respective guide rods 17 and adjustment bolt 16 should be great enough to allow free movement, but close enough to prevent unnecessary looseness during the operation of the patellar resection guide and to maintain the plates in their parallel orientation as they are drawn together.

The cradle supports 30, 31 are on opposite ends of the cradle 12 and desirably are parallel to each other; that is, they have outer surfaces 48, 50 that are congruent to each other. Support surfaces 48, 50 may be slightly curved (concave outwardly), but preferably are straight in the medial-lateral direction to define between them a reference plane. They are used to suspend the quadriceps tendon and patella ligament in a plane which is parallel to but not necessarily coplanar with the desired resection plane. The distance between cradle supports 30, 31 is sufficient to accommodate between them a human patella with the posterior surfaces of the attached quadriceps tendon and patellar ligament resting on the cradle supports. Desirably, the spacing between the cradle supports is slightly greater than the superior-inferior dimension of the patella so that when the patella is drawn between the cradle supports as by flexing the knee, the supports do not contact the patella itself. In a preferred embodiment, the end-to-end dimension of the gripping plates is sufficiently small as to enable the plates to fit between cradle supports separated by varying distances. In this manner, the resection guide is modular in construction so that a cradle of any particular chosen size can be assembled with a standard sized pair of gripping plates. Of course, if desired, gripping plates of varying dimensions can be supplied as well.

Figure 6:
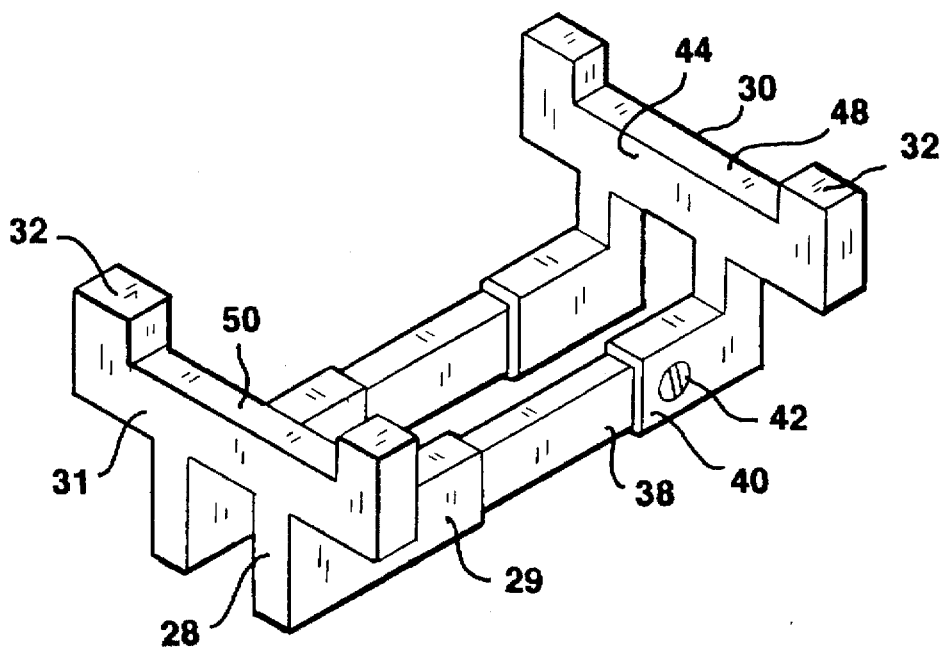
FIG. 6 is a perspective view of a modified cradle.

While is desired that the gripping means be so oriented as to grip the lateral and medial surfaces of a patella received between the cradle support surfaces, the gripping elements may instead be provided by the cradle structure so that the cradle supports may be moved toward each other to capture between them the patella. FIG. 6 shows an embodiment in which the frame structure supporting the cradles is itself adjustable to enable the cradles to move toward and away from each other while maintaining their mutually parallel orientation. In FIG. 6, each of the cradle cross members 29 is formed with telescoping ends, one end 38 of each cross member being telescopingly received in the adjacent hollow end 40. Set screws 42 may be used to join the ends 38, 40 together once the correct length of these members has been set. The confronting surfaces 44, 46 of the respective cradle supports 30, 31 may serve as gripping surfaces (and may be provided with teeth or the like) to grip between them a patella, the quadriceps tendon and patellar ligament of which rest against the outer support surfaces 48, 50 of the cradle supports. Saw blade guiding surfaces or slots (not shown) may be provided to guide a saw blade.

Figure 7:
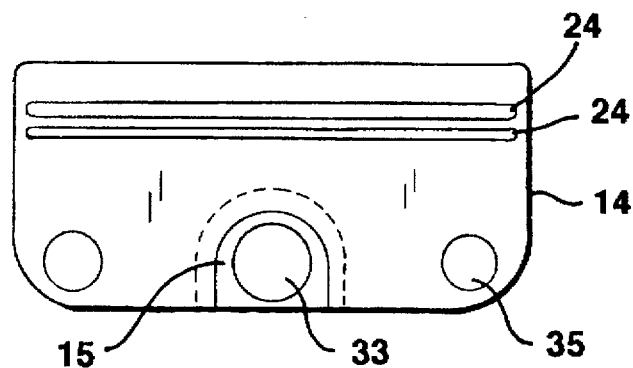
FIG. 7 is a front end view of an embodiment of a bone guide plate of the patellar resection guide of FIG. 1 with a plurality of saw blade slots.
Figure 8:
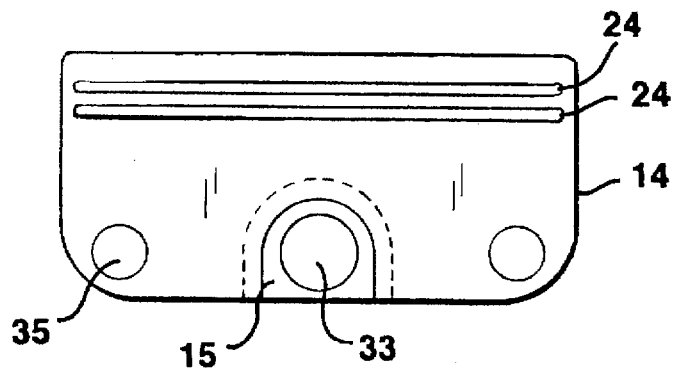
FIG. 8 is a front end view similar to FIG. 7 showing a bone guide plate with an alternate arrangement of saw blade slots.

FIGS. 7 and 8 show an embodiment of the blade guide plate 14 having a plurality of saw blade guide slots 24. The saw blade slots 24 as shown illustrate how the invention is able to accommodate various depths of resection the surgeon may require due to differing sized patellae or conditions. In addition to providing a variety of resection depths, the blade guide plate 14 must also provide stability and orientation to the oscillating saw blade to ensure that the resection is done in the proper plane. This is accomplished by employing a slot depth sufficient to prevent significant tilting of the saw blade during the resection procedure. Slot depth dimensions of approximately 0.25 inch to 0.5 inches have been shown to be adequate for this purpose. These dimensions, however, are intended to be illustrative and not limiting.

Although the invention is described primarily with respect to resection using a bone saw to form a planar posterior surface on the patella, it will be understood that the patella may be resected by forming holes, grooves or other shapes in or on the posterior patellar surface. The end-to-end length of the blade guide plate 14 and stop plate 20 are less than the distance between the cradle supports 30, 31 to enable blade guide plate 14 and stop plate 20 to move toward each other sufficiently close to effectively grasp the patella during the resection procedure. It is contemplated and within the scope of this invention to manufacture the cradle 12 in various sizes, to be able to accommodate differently sized patellae. Similarly, blade guide plate 14 and stop plate 20 would be sized to be able to be compatible with the contemplated variously sized cradles 12.

Figure 9:
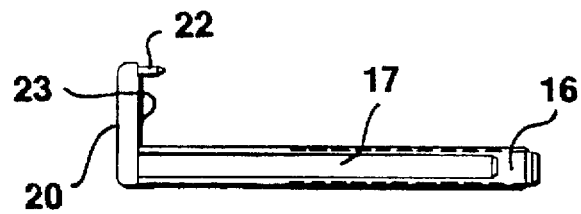
FIG. 9 is a side view of a stop plate showing an adjustment bolt and guide rods.
Figure 10:
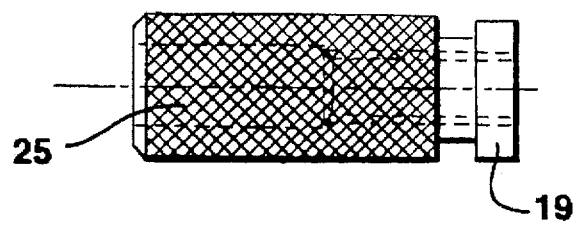
FIG. 10 is a side view of a captured adjustment nut employed in the patellar resection guide of FIG. 1.

FIG. 9 shows the stop plate 20 with rigidly affixed guide rods 17 and adjustment bolt 16. When assembling the patellra resection guide 10, the stop plate 20, adjustment bolt 16 and guide rods 17 are first fitted through the apertures 36, 34 in the cross members 29 of the cradle 12. Following this, the captured nut 19 is fitted into the T shaped channel 15 of the blade guide plate 14. The captured nut 19 is best shown in FIG. 10, and the T shaped channel 15 of the bone guide plate 14 is best shown in FIG. 11. Next, the adjustment bolt 16 and guide rods 17 are placed through the apertures 33, 35 of the blade guide plate 14. It is necessary to align the captured nut 19 with the adjustment bolt 16 and then turn the captured nut 19 in a direction corresponding with advancing the blade guide plate 14 toward the stop plate 20. At this point, assuming it is properly sterilized, the patellar resection guide 10 is assembled and ready for use.

It is also contemplated to assemble and use the blade guide plate 14 and stop plate 20 without the cradle 12. This embodiment would give the surgeon somewhat greater flexibility in resecting the patella, but a lesser degree of precision.

Figure 12:
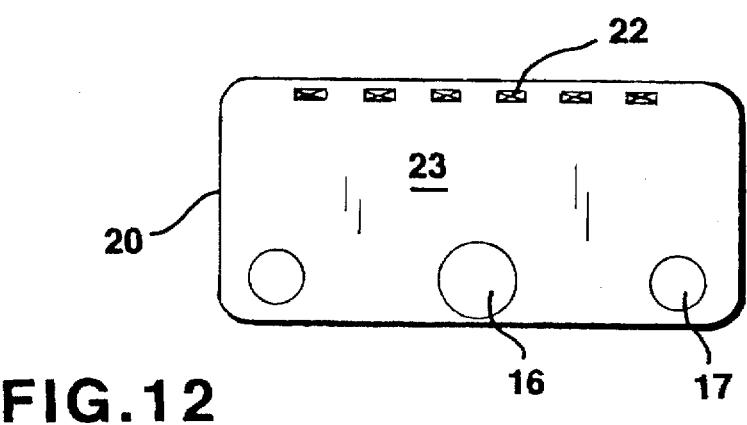
FIG. 12 is a front view of the stop plate of the patellar resection guide of FIG. 1.

FIG. 12 shows the stop plate 20 and affixed adjustment bolt 16 and guide rods 17 prior to assembly.

The preferred material for all components of this invention is stainless steel. Other materials, including but not limited to other metals and metal alloys, plastics and composite materials, are also anticipated as being appropriate.

Figure 13:
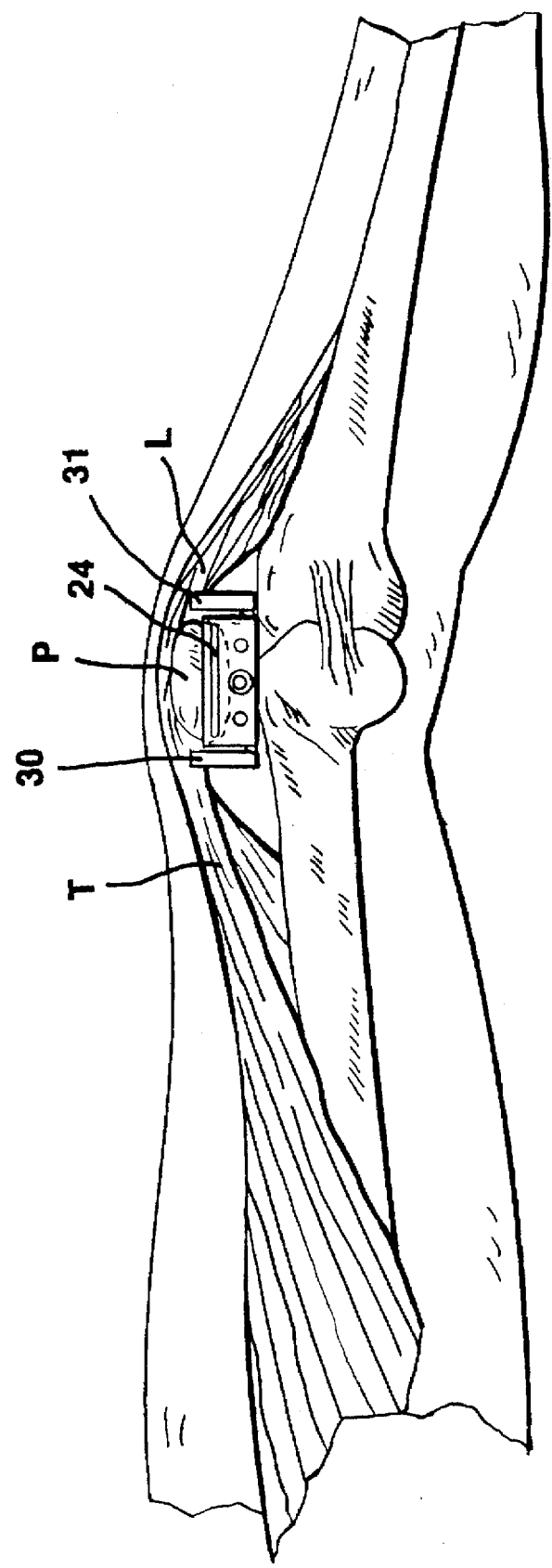
FIG. 13 shows a diagrammatic side view of the patellar resection guide of FIG. 1 as used during a surgical procedure.

FIG. 13 shows the patellar resection guide 10 as it would be used during an actual procedure. It can be seen that the quadriceps tendon T and patellar ligament L are suspended in a plane defined by first cradle support 30 and second cradle support 31 of the cradle 12. The patella P is secured in the patellar resection guide 10 by means of force exerted by the gripping surfaces 21, 23. Flexion of the knee joint causes the quadriceps tendon T and patellar ligament L to press against the cradle supports, properly orienting the patella between the gripping plates before they are moved to their gripping position. The procedure for using the guide is discussed in detail below.

Figure 14:
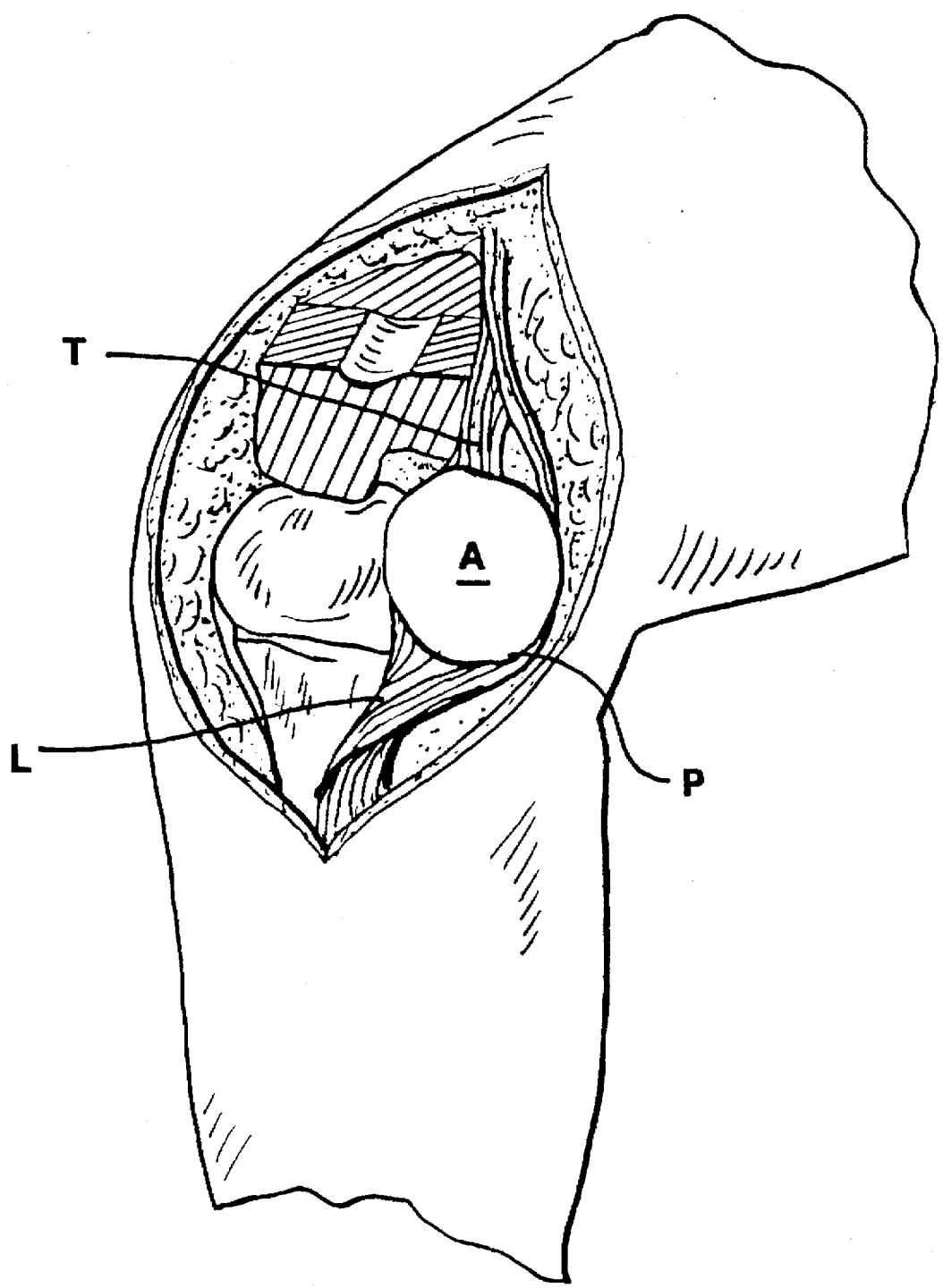
FIGS. 14 and 15 are diagrammatic views showing steps in a surgical method using the resection guide of FIG. 1.

In a typical procedure for using the patellar resection guide, the surgeon first creates a longitudinal incision medial to the patella to expose the patella and quadriceps mechanism which includes the quadriceps tendon and patellar ligament. This is done to a degree allowing exposure of sufficient quadriceps tissue and patellar ligament to permit the surgeon to rotate the patella laterally prior to insertion of the resection guide 10. As shown in FIG. 14, the patella is disarticulated from the femur and is turned upside down, that is, it is rotated laterally through about 180°, resulting in the articular surface A of the patella facing forward or anteriorly (that is, outwardly).

At this point, the surgeon places the patellar resection guide 10 over the exposed articular surface of the patella, with the cradle supports adjacent the quadriceps tendon and patellar ligament. The patella and patellar resection guide together are re-rotated medially through about 180° to position the resection guide 10 between the patella and the femur. The knee is slightly flexed to tension the quadriceps mechanism, thereby applying a compressive load between the patella and femur. This draws the quadriceps ligament and patella tendon firmly into the cradle supports of the guide 10. When the patellar tendon and ligament are firmly seated in the cradle 12, as shown in FIG. 13, the patella is positioned in a repeatable or reference position with respect to the reference plane defined by the cradle support surfaces. This position is defined by the posterior aspect of the inferior and superior margins of the ligament and tendon attachment of the patella, respectively, which, when they are firmly seated against the support surfaces, lie in the reference plane defined by the cradle supports. This plane is typically perpendicular to the resultant forces acting on the patella and is parallel to the plane of the intended resection. The preferred orientation of the patellar resection plane is perpendicular to the resultant forces acting across the patellar femoral joint. While maintaining slight flexion on the knee, the captured nut 19 is rotated in a direction causing the blade guide plate 14 and stop plate 20 to move closer together. The blade guide plate 14 and stop plate 20 move in a mediolateral sense. This procedure is followed until the patella is securely gripped in the patellar resection guide 10.

Figure 15:
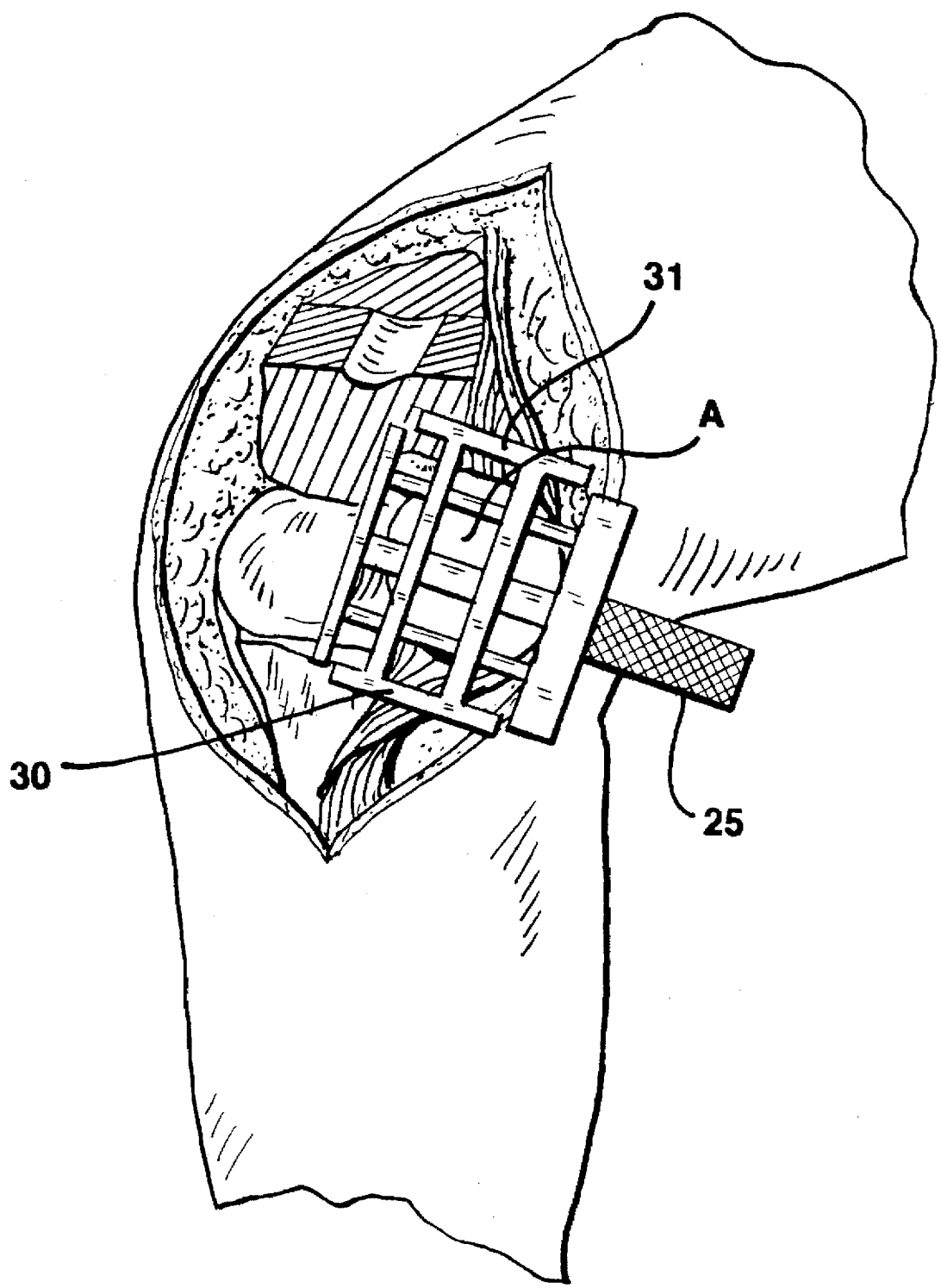

With the patella thus firmly gripped, the patella and resection guide are again rotated laterally to again orient the resection guide 10 and articular surface of the patella outwardly, as shown in FIG. 15. The surgeon places an oscillating bone saw of a type commonly known into the saw blade slot 24 and advances the saw to resect the patella. The articular surface of the patella is resected at a level posterior to the ligament and tendon insertions. This permits the surgeon to resect only bone tissue, avoiding the ligaments and tendons. The depth of resection beneath the ligament and tendon insertion levels may vary depending on surgeon preference. In one embodiment the invention accommodates for this requirement by providing multiple saw blade slots 24 at differing levels in the blade guide plate 14. In one embodiment, a level of one millimeter is used. The level may range from a level matching that of the ligament and tendon insertion level, to a level posterior to it, or anterior to it.

Following resection, the patellar resection guide 10 is removed. After removal of the guide 10, the surgeon will follow established procedures to further prepare the resected articular surface of the patella to accept a patellar button or other implant.

While a preferred embodiment of the present invention has been described, it should be understood that various changes, adaptations, and modifications may be made without departing from the spirit of the invention and the scope of the claims.

I claim:

1. A patella resection guide comprising a body, a pair of parallel cradle surfaces carried by the body and spaced in the superior-inferior direction so as to encounter and support respective posterior surfaces of the quadriceps tendon and the patella ligament of a patella received between the cradle surfaces, the cradle surfaces defining a reference plane, and means for resecting the patella at a desired orientation with respect to said reference plane.

2. The patella resection guide of claim 1 wherein said cradle surfaces are straight in the lateral-medial direction.

3. The patella resection guide of claim 1 wherein said cradle surfaces are curved in the lateral-medial direction.

4. The patella resection guide of claim 1 wherein said body includes adjustment means enabling the cradle surfaces to be moved toward and away from each other while preserving their parallel orientation.

5. The patella resection guide of claim 1 wherein the cradle surfaces each include a straight central portion and end portions angled from the central portion to retain between them and in contact with the central portion the posterior surfaces of the quadriceps tendon and patellar ligament, respectively.

6. The patella resection guide of claim 1 including a pair of gripping elements carried by the body and movable toward each other to firmly grip a patella between them.

7. The patella resection guide of claim 6 wherein said gripping elements define between them a plane parallel to the plane defined by said cradle surfaces.

8. The patella resection guide of claim 6 including manually operable means for controllably drawing said gripping surfaces toward each other.

9. The patella resection guide of claim 8 wherein said body includes a plurality of guide rods extending between the gripping elements and joining the gripping elements to the body and enabling one gripping element to slide along the rods toward the other gripping element.

10. The patella resection guide of claim 9 wherein said means for drawing said gripping elements toward each other comprises a first threaded element carried by one of the gripping elements and a second threaded element carried by the other gripping element and threadingly engaging the first threaded element, one of said threaded elements being rotatable with respect to the other to draw the gripping elements toward each other.

11. A patella resection guide comprising gripping means including a pair of gripping elements having respective parallel confronting gripping surfaces spaced to receive and grip a patella between them, means for supporting said elements and retaining their gripping surfaces in parallel while enabling them to be advanced toward each other to grip a patella between them, at least one of the gripping elements including saw guide means for guiding a bone saw during resection of a patella gripped between the gripping surfaces.

12. The patella resection guide of claim 11 including means for controllably drawing said gripping elements toward each other.

13. The patella resection guide of claim 12 wherein said means for drawing said gripping elements toward each other comprises a first threaded element carried by one of the gripping elements and a second threaded element carried by the other gripping element and threadingly engaging the first threaded element, one of said threaded elements being rotatable with respect to the other to move the gripping elements toward and away from each other.

14. The patella resection guide of claim 13 wherein one of said threaded elements comprises a rod having a threaded portion along its length and the other threaded element comprises an interiorly threaded nut, one of the rod and nut being non-rotatably attached to one of the gripping elements and the other of the rod and nut being rotatably mounted to the other gripping element.

15. The patella resection guide of claim 14 wherein one of said gripping elements is recessed to rotatably receive said nut.

16. The patella resection guide of claim 15 wherein the rotatable nut includes an outwardly extending manually rotatable adjustment knob.

17. The patella resection guide of claim 11 wherein said means for supporting said gripping elements includes a plurality of guide rods extending between the gripping elements and enabling one gripping element to slide along the rods toward the other gripping element.

18. The patella resection guide of claim 11 wherein one or both of said gripping surfaces include a plurality of teeth oriented to contact and grip a patella received between the gripping elements.

19. The patella resection guide of claim 11 wherein said saw blade guide comprises one or more saw blade-receiving slots formed in one or both of said gripping elements.

20. The patella resection guide of claim 11 including means defining a pair of spaced, parallel, transversely extending cradle surfaces positioned adjacent ends of said gripping elements to encounter and support posterior surfaces of the quadriceps tendon and the patella ligament, respectively, of a patella received between the gripping elements.

21. A patella resection guide comprising a pair of gripping elements having respective confronting gripping surfaces spaced to receive a patella between them, means defining a pair of spaced, parallel, transversely extending cradle surfaces positioned adjacent ends of said gripping elements to encounter and support posterior surfaces of the quadriceps tendon and the patellar ligament, respectively, of a patella and to accurately position a patella received between the gripping surfaces, means for controllably drawing said gripping elements toward each other, and means for supporting said gripping elements to maintain their gripping surfaces in a parallel orientation while the gripping elements are drawn toward each other to grip a patella between them, at least one of the gripping elements including saw guide means for guiding a bone saw during resection of a patella gripped between the gripping elements.

22. A patella resection guide comprising a body, a pair of parallel cradle surfaces carried by the body and spaced in the superior-inferior direction so as to encounter and support respective posterior surfaces of the quadriceps tendon and the patella ligament of a patella received between the cradle surfaces, gripping means comprising gripping elements having patella-gripping surfaces in a confronting orientation, said gripping elements being carried by said body and movable toward each other while maintaining the confronting orientation of said gripping surfaces to firmly grip between them lateral and medial surfaces of a patella supported between said cradle surfaces, manually operable means for controllably drawing said gripping elements toward each other, and a saw guide carried by the gripping means for guiding a bone saw during resection of a patella gripped by the gripping means.

23. Method for resetting a patella, comprising:

a. surgically exposing the patella, quadriceps tendon and patellar ligament;

b. providing a resection guide having parallel cradle surfaces spaced to encounter posterior surfaces of the quadriceps tendon and the patellar ligament of the patella to support a patella in a fixed orientation with respect to a reference plane defined by said cradle surfaces, means for gripping and holding the patella in said fixed orientation, c. supporting the patella in said resection guide with said cradle surfaces contacting and supporting respectively the posterior surfaces of the quadriceps tendon and the patellar ligament of the patella, d. gripping the patella in said orientation; and e. resecting the patella.

24. The method of claim 23 including, before step d, flexing the knee joint to draw the quadriceps tendon and patellar ligament tightly against said cradle surfaces.

25. The method of claim 23 including, before step c, the step of rotating the patella to expose its articular surface.

26. The method of claim 25 including, before step d, re-rotating the patella to place the resection guide between the patella and femur and flexing the knee joint to draw the quadriceps tendon and patellar ligament tightly against said cradle surfaces.

27. The method of claim 23 or claim 26 including the step, before step e, of rotating the patella to expose its articular surface to facilitate said resection step.

28. The method of claim 23 wherein said resection guide includes a bone saw guide, including the step of resecting the patella in a plane in a resection operation in a plane having a predetermined orientation to said reference plane.

29. Method for resecting a patella, comprising:

a. surgically exposing the patella, quadriceps tendon and patellar ligament;

b. providing a resection guide having parallel cradle surfaces spaced to encounter posterior surfaces of the quadriceps tendon and the patellar ligament of the patella to support a patella in a fixed orientation with respect to a reference plane defined by said cradle surfaces, the resection guide having gripping surfaces carried in opposed, confronting orientation by gripping elements that are movable toward each other to encounter and grasp the patella, and a saw guide, c. supporting the patella in said resection guide with said cradle surfaces contacting and supporting posterior surfaces of the quadriceps tendon and the patellar ligament, respectively, of the patella, d. flexing the knee joint to draw the quadriceps tendon and patellar ligament tightly against said cradle surfaces to position the patella in said fixed orientation, e. drawing said gripping elements together while maintaining the opposed, confronting orientation of the gripping surfaces to grip lateral and medial surfaces of the patella, and f. resecting the patella with a saw guided by the saw guide.

* * * * *